United States Patent [19]

Schachar

[11] Patent Number: 4,564,637
[45] Date of Patent: Jan. 14, 1986

[54] METHOD FOR MAINTAINING CORNEAL SHAPE AFTER RADIAL KERATOTOMY

[76] Inventor: Ronald A. Schachar, P.O. Box 145, Denison, Tex. 75020

[21] Appl. No.: 294,158

[22] Filed: Aug. 19, 1981

[51] Int. Cl.$^4$ .................... A61K 31/19; A61K 31/135; A61K 31/557
[52] U.S. Cl. .................................... 514/573; 514/654; 514/912
[58] Field of Search ................................ 424/311, 317

[56] References Cited

U.S. PATENT DOCUMENTS

| 3,852,337 | 12/1974 | Bergstrom et al. | 424/311 |
| 3,928,425 | 12/1975 | Pike et al. | 424/311 |
| 4,029,814 | 6/1977 | Bundy | 424/308 |
| 4,254,145 | 3/1981 | Birnbaum | 424/311 |
| 4,510,145 | 4/1985 | Schacher | 514/415 |

OTHER PUBLICATIONS

Invest. Ophth. 11, 1022 (1972).
Chem. Abst. 77, 14,651(q), (1972)–Chiang et al.
Chem. Abst. 81, 99776(q), (1974)–Takats et al.
Chem. Abst. 91, 172,836(x), (1979)–Izawa et al.

*Primary Examiner*—Douglas W. Robinson
*Attorney, Agent, or Firm*—Vorys, Sater, Seymour & Pease

[57] ABSTRACT

The relatively flattened shape of a cornea following radial keratotomy is maintained by administering to the eye a chemical compound which effectively increases intraocular pressure therein.

7 Claims, No Drawings

METHOD FOR MAINTAINING CORNEAL SHAPE AFTER RADIAL KERATOTOMY

BACKGROUND OF THE INVENTION

1. Field of the Invention

This invention relates to a method of maintaining the shape of the cornea of the eye in a flatter than normal configuration after radial keratotomy, and more particularly to maintaining such shape by increasing and controlling intraocular pressure within the eye.

2. Description of the Prior Art

Recently a surgical procedure has been proposed for the surgical correction of complex myopic astigmatism by anterior keratotomy (see Fedorov, S.N., et al., *Oftalmologischeskii Zhurnal* (Odessa) 34(4):210-2(1979); Utkin, V. F., *Vestnik Oftalmologii* (Moskva), (2):21-4(1979)). This procedure involves making a series of radial non-penetrating incisions on the periphery of the cornea, whereby the cornea is weakened so as to induce an alteration in its curvature. Consequently, the cornea becomes flatter, thereby altering its optical power and substantially correcting the myopic condition. In the initial stages of this procedure the flattening of the cornea occurs partially because of edema, i.e., the absorption of water into the cornea which causes it to swell. Within approximately two weeks the edema subsides, but a regression of the flattened condition of the cornea occurs over about four months. Since it is the flattening of the cornea which effects correction of the myopic condition, the post-operative process of regression is counterproductive to the intended result of the procedure.

Hence a need has continued to exist for a method for arresting or at least impeding the post-operative regression in radial keratotomy.

SUMMARY OF THE INVENTION

Accordingly, it is an object of this invention to provide a method for preventing post-operative regression of the beneficial effects of radial keratotomy.

A further object is to maintain the altered shape of the cornea produced by radial keratotomy.

These and other objects of the invention as will become apparent from the following description are attained by the method of this invention which comprises elevating the intraocular pressure of an eye above normal values after radial keratotomy and maintaining the intraocular pressure at an elevated level for a sufficient period of time to permit the corneal incisions to heal, whereby the cornea is maintained in a predetermined shape. The intraocular pressure is elevated above its normal level and maintained at this elevated level by administration to the eye of an effective amount of an intraocular pressure-increasing chemical compound.

DETAILED DESCRIPTION OF THE PREFERRED EMBODIMENTS

For purposes of this specification and claims, an effective amount of intraocular pressure-raising compound is that amount which raises the intraocular pressure to a sufficient extent to maintain the desired flattened shape of the cornea, with corresponding correction of the patient's myopia. The practitioner will understand that the dose may have to be varied from individual to individual and from time to time in a single individual in order to maintain the elevation of intraocular pressure required to achieve the desired results. The required dose can be easily determined by its effect. The intraocular pressure can be measured by standard tonometry procedures. The shape of the cornea and the refractive ability of the eye can be monitored by procedures which are well known in the art. According to the invention, an effective amount of intraocular pressure-raising compound is administered to the eye after the radial keratotomy procedure has been performed and the administration is continued in order to maintain the intraocular pressure at the level effective to maintain the preselected flattened shape of the cornea until the cornea has substantially healed. The administration is then discontinued to allow the intraocular pressure to return to normal levels. It will be understood by the skilled practitioner that it is also within the scope of the invention to administer the intraocular pressure-increasing compound before the keratotomy procedure is performed if it is indicated by the condition of the patient in order to produce the desired effect.

The substance used as an agent effective to increase intraocular pressure may be any compound which has the requisite property of raising intraocular pressure when administered to humans or mammals. Preferred compounds include prostaglandin-$E_1$, prostaglandin-$E_2$, and beta-phenylethylamine. A discussion of the use of prostaglandins in the eyes of humans is found in *Investigative Ophth.*, Vol. 11, p. 1022 (1972).

The intraocular pressure-increasing agents used in practicing the method of this invention may be applied to the eyes by any known means. In preferred form they are applied topically to the eye, e.g., by instillation of a solution of the active ingredient in a suitable non-toxic ophthalmic vehicle. Essentially any conventional solution forming technique may be utilized in preparing the ophthalmic solutions of this invention. Aqueous ophthalmic solutions may be formulated, for example, in accord with the procedures set forth in Chapter 83 of Remington's Pharmaceutical Sciences, 14th Edition, Mack Publishing Company. As such, they are sterile and may contain bacteriological preservatives to maintain sterility during use.

For most purposes, the addition of benzalkonium chloride to the ophthalmic solution provides the desired biocidal preservative effect. However, additional biocides may be incorporated if desired. For example, it is generally desirable to incorporate a suitable chelating agent to enhance the preservative effect of the benzalkonium chloride. Suitable chelating agents include di-, tri-, or tetrasodium ethylene diamine tetracetate, also known as edetates, with disodium edetate being a preferred ingredient. Other diocides that may be optionally included in the ophthalmic solution include thimerosal, phenylmercuric nitrate, chlorobutanol, and sorbic acid.

For most ophthalmic uses it is desirable that the ophthalmic solution is isotonic. Conventionally, ophthalmic solutions are rendered isotonic by addition of suitable salts, for example, sodium chloride, potassium chloride, calcium chloride, magnesium chloride, and various nitrates, citrates, acetates, etc. Preferably, monovalent salts such as sodium chloride and the like are added in an amount sufficient to give a freezing point depression or osmotic pressure equivalent to that provided by 0.5% to 1.5% sodium chloride.

If desired, the ophthalmic solutions utilized in this invention may be adjusted in pH by one or more of the acids or bases known for use in ophthalmic solutions. The ophthalmic solutions may be maintained in an acidic, basic, or neutral condition by use of buffers commonly employed in ophthalmic solutions. The use of suitable acids, bases and buffering systems to establish a pH within the range of from about 3.0 to about 8.5 is well known and requires no further description. Typically, the pH of the ophthalmic solutions utilized in this invention is between about 5.0 and 8.0, preferably between about 6.0 and about 7.5.

The viscosity of the ophthalmic solutions used in the present invention may be adjusted to a point within the range of from about 1 cps to about 25 cps at 25° C. (The viscosity of the ophthalmic solutions is measured on a Wells-Brookfield Microviscometer (cone and plate) Model LVT.) Such an adjustment can be made by inclusion of water-soluble viscosity building agents. Suitable viscosity building agents include natural gums, such as guar gum and gum tragacanth, gelatin, starch derivatives, polymeric glycols, and cellulosic polymers, such as hydroxyethyl cellulose, hydroxypropylcellulose, methylcellulose, hydroxypropylmethylcellulose, and carboxymethylcellulose. Viscosity building agents, when used, are present in such ophthalmic solutions at a level of from about 0.001% to about 1.0% by weight. The exact percentage depends on the molecular weight of the polymer used which is within the skill of the art. When a viscosity building agent is utilized, the viscosity of the ophthalmic solution may be between about 1 cps and about 25 cps, preferably between about 3 cps and about 15 cps.

Ointments may also be employed as vehicles for the active ingredients used in the treatment of this invention. Such ointments may be prepared by utilizing known pharmaceutical techniques with conventional petrolatum vehicles.

The ophthalmologically effective amounts of intraocular pressure-increasing agent used in the method this invention will vary depending on the potency of the selected active ingredient. The amounts may be readily determined by monitoring the effect of the administered dose as pointed out above. Typically, however, the concentration of active ingredient in an aqueous solution used in the method of this invention will be between 5 mg/5 ml to 50 mg/5 ml of the solution. Such a solution will be topically adminstered to humans in a dosage of 1-2 drops per eye every four hours during the awake periods of the healing process, i.e., for about four months. Preferably, the application of the solutions utilized in this invention will be in drop form in the manner typically used to apply eye drops. Thus, the normal squeeze-type liquid drop application devices are perfectly suitable for use in applying the ophthalmic solutions of this invention to an eye intended for treatment.

It should be understood that this invention may be embodied in other specific forms without departing from its spirit or essential characteristics. Accordingly, the present embodiments are to be considered in all respects illustrative and not restrictive, the scope of the invention being indicated by the appended claims rather than by the foregoing description, and all claims which come within the meaning and range of equivalency of the claims are intended to be embraced therein.

I claim:

1. A method for effecting and maintaining the curvature of the cornea of an eye in a predetermined curvature after radial keratotomy surgery wherein the cornea has at least one radial incision comprising elevating the intraocular pressure of said eye above normal levels by directly administering to said eye an amount of an intraocular pressure-raising compound effective to raise the intraocular pressure above the normal value, and maintaining the intraocular pressure at an elevated level for a period of time to permit the corneal incision of said radial keratotomy to heal, whereby the cornea is maintained in said predetermined curvature.

2. The method of claim 1 wherein said compound is selected from the group consisting of prostaglandin-$E_1$, prostaglandin-$E_2$, and bets-phenylethylamine.

3. The method of claim 1 wherein said compound is administered topically.

4. The method of claim 3 wherein said compound is administered in aqueous solution.

5. The method of claim 4 wherein said solution is isotonic and contains a biocidal preservative.

6. the method of claim 4 wherein said solution contains about 5 mg/5 ml to 50 mg/5 ml of said compound.

7. The method of claim 1 wherein said compound is selected from the group consisting of prostaglandin-$E_1$ and prostaglandin-$E_2$.

* * * * *